United States Patent [19]

Locker

[11] 4,327,575

[45] May 4, 1982

[54] MONITORING APPARATUS AND METHOD FOR TOXIC VAPORS

[76] Inventor: Laurence D. Locker, 201 NE. 2nd St., Pompano Beach, Fla. 33060

[21] Appl. No.: 133,249

[22] Filed: Mar. 24, 1980

[51] Int. Cl.[3] ............................................. G01N 31/06
[52] U.S. Cl. .......................................... 73/23; 422/88
[58] Field of Search .................... 73/23, 421.5; 422/88

[56] References Cited

U.S. PATENT DOCUMENTS 3,950,980  4/1976  Braun et al. ............................. 73/23
3,992,153  11/1976  Ferber et al. ......................... 422/88
4,040,805  8/1977  Nelms et al. ............................. 73/23
4,046,014  9/1977  Boehringer et al. ........... 73/421.5 R Primary Examiner—Anthony V. Ciarlante
Attorney, Agent, or Firm—D. Paul Weaver

[57] ABSTRACT

An apparatus and method for measuring toxic vapors through the use of a two chamber sensing device is presented wherein a first chamber contains an adsorbent for materials not to be monitored but which interfere with the monitoring process and the second chamber contains a material that collects the substance to be analyzed.

17 Claims, 9 Drawing Figures

U.S. Patent  May 4, 1982  Sheet 1 of 4  4,327,575

MONITORING APPARATUS AND METHOD FOR TOXIC VAPORS

TECHNICAL FIELD

This invention relates to a means to monitor substances in a gaseous or vaporous state in an atmosphere containing additional gases or vapors which affect the reliability of the basic sensing means.

BACKGROUND OF PRIOR ART

Exposure of personal to hazardous materials in the atmosphere has long been a serious problem in many industries. As our knowledge increases, it becomes increasingly apparent that a wide variety of hazardous substances are present in the air we breathe and constitute major occupational hazards in numerous industries.

To counter the effect of hazardous materials in the atmosphere, numerous attempts have been made to provide personal monitoring devices which will supply an indication as to the extent of exposure of individuals wearing the badges. One such device is the "Personal Monitoring Device, Or Dosimeter, For Measuring Exposure Of Personal To Organic Vapors", U.S. Pat. No. 4,040,805 issued to L. Nelms et al. This patent discloses a personal monitoring device which is calculated to meet the National Institute for Occupational Safety and Health requirements by providing an indication as to the amount of vinyl chloride that a person has been exposed to within a work establishment. This device provides a fairly reliable means to determine certain pollutants in the atmosphere so long as the material used to adsorb the pollutants for subsequent analysis is maintained free of material which will interfere with the analysis and affect the ability of the adsorbing material to function in accordance with a desired, predetermined reaction rate.

D. Braun, U.S. Pat. No. 3,950,980 for "Vapor Sampling Device" is another U.S. Patent which attempts to provide a monitoring means to determine constituents in an ambient gas mixture. This patent and Braun's U.S. Pat. No. 3,924,219 on "Gas Detector Device" teach the principle of a detector material which reacts with a component to be monitored in a predetermined fasion. The reaction is regulated by controlling the gas contact with the adsorbing material through the use of porous gas flow attenuating means and channels. This approach eliminates variances in the monitoring system caused by velocity and incident angle variations of the impinging gas with respect to the sensing material but it fails to compensate for materials such as $Cl_2$ in the atmosphere which are not being measured but which affect the measurement of the substance of interest.

A still further example of prior art gas monitoring means may be found in R. Goldsmith U.S. Pat. No. 3,985,017 on "Gaseous Contaminate Dosimeter And Method" which uses techniques similar to those of the Braun devices in that a membrane controls flow of the gas toward an adsorber but, like all of the known prior art devices, it fails to overcome the problems resulting from atmospheric constituents which interfere with the adsorption rate of the detector material.

OBJECTIVES OF THE INVENTION

In view of the obvious inability of the prior art monitoring devices to compensate for the presence in an atmosphere being monitored of substances which are not of interest but which affect the monitoring device, it is a primary objective of the present invention to provide a personal monitoring device for toxic vapors which will not be affected by constituents in the atmosphere other than the actual substance for which a measurement is being made.

A further objective of the present invention is to provide a monitoring system comprised of a chamber containing an adsorbent for the substance to be monitored in combination with a second chamber containing a means to prevent substances which will affect the adsorbent but which are not substances to be monitored from reaching the adsorbent.

A still further objective of the present invention is to provide a personal monitoring device for toxic vapors wherein the atmosphere being monitored must first pass through a screening zone which eliminates preselected substances but permits the passage of the substance to be measured into a monitoring chamber.

A further objective of the present invention is to provide a personal monitoring device which reliably produces repeatable measurements, is not affected by substances other than that being monitored, and is inexpensive to produce and analyze after exposure.

The foregoing and other objectives of the present invention will become apparent in view of the specification and drawings which follow.

SUMMARY OF THE INVENTION

Presented hereby is a personal monitoring device comprised of a material which collects a substance to be analyzed. The material is positioned within a container and insulated from ambient atmosphere by an adsorbent which adsorbs substances which will affect the functioning of the collecting substance but will pass and not adsorp the substances to be collected.

The substance collector is analyzed after a predetermined period of exposure by any of the well known techniques for determining the amount of substance collected, such as thermal desorption of the substance from the collector or solvent extraction and analyzing the desorbed material with a chromatographic detector.

DESCRIPTION OF THE INVENTION

Figure 1:
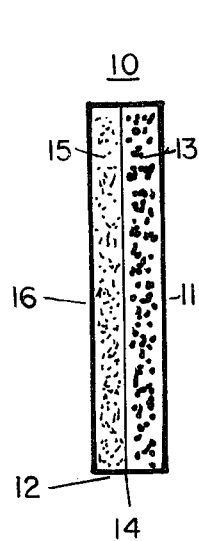
FIG. 1 is a cutaway view of an embodiment of the present invention illustrating first and second containers for an adsorbent and collector material.

In its simplest form, the invention is comprised of a container 10 (FIGS. 1 and 2) comprised of a gas impervious back 11 and four sides 12. The relatively shallow container formed of the gas impervious members 11 and 12 functions as a receptacle for a collecting agent 13 which is positioned in the section of the container against the back portion 11.

The collecting agent 13 is the primary adsorbent of the system. It is held in place by a separator 14 which is permeable to the substance to be collected. The separator and sides form an outer chamber in which an isolating adsorbent 15 is placed. The isolating adsorbent 15 adsorbs substances in the atmosphere which would affect the operation of the primary adsorbent 13 but it will pass the material to be collected.

The isolating adsorbent 15 is retained in the container by a porous membrane 16.

Figure 3:
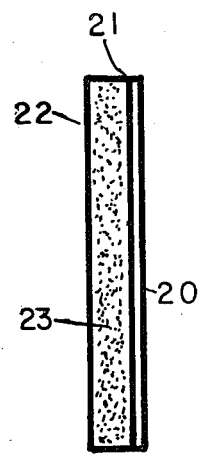
FIG. 3 is a side, cutaway view of an embodiment of the present invention illustrating the use of a solid collector material.

FIG. 3 is a further embodiment of the subject invention wherein the primary adsorbent is a flat surface. A gas impervious substrate 20 supports a metal surface 21 which functions as a collector or adsorber for the material to be detected. A container 22 encloses the metal surface and houses a substance 23 which functions to adsorb materials other than the material to be monitored and thus prevents them from being adsorbed by the metal surface and affecting the operation of the device.

Figure 2:
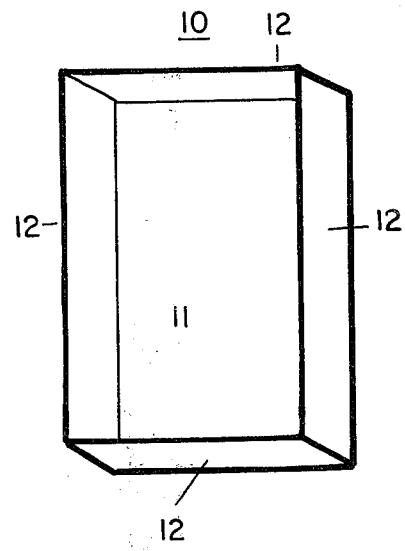
FIG. 2 is a front view of the embodiment illustrated in FIG. 1.
Figure 4:
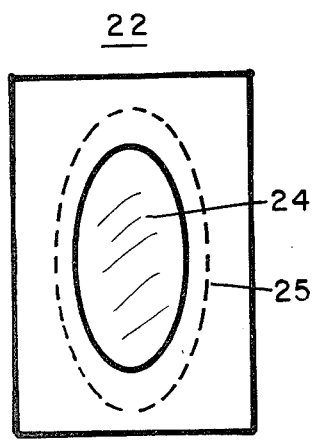
FIG. 4 is a front view of the embodiment illustrated in FIG. 3.

FIG. 4 illustrates a cover 22 which has an opening 24 that is sealed with a porous membrane 25. The cover 22 may be used with the embodiments of FIG. 2 or 3. The rate of adsorption or collection by surface 21 of FIG. 3 or primary adsorbent 13 of FIG. 1 is controlled by varying the area of the opening or the porosity of the membrane or both techniques.

The concept of a variable opening and controllable porosity membrane may be used in any of the embodiments disclosed or anticipated by this specification.

A further embodiment of the present invention includes a selective porous membrane wherein certain undesirable constituents of the gas being monitored are prevented from entering the monitoring chambers and thus performs a function similar to the protective adsorbent 15 or 23 in the previously described embodiments.

Figure 5:
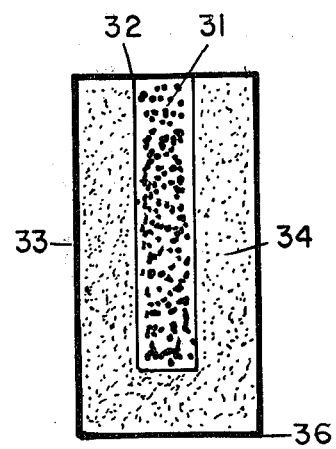
FIG. 5 is a side, cutaway view of an embodiment of the present invention wherein the collector is suspended within a container of adsorbent materials.
Figure 6:
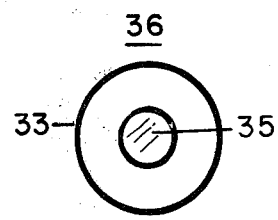
FIG. 6 is a top view of the embodiment of the present invention illustrated in FIG. 5.

FIG. 5 is a still further embodiment of the present invention wherein the collection materials 31 may be in the form of a solid rod or a granular substance within a tubular, permeable container 32. The collecting material 31 is suspended within a gas permeable tube 33 which is packed with a granular adsorbing material 34 which functions to prevent materials in the atmosphere which will affect the functioning of the collector from reaching the collector. If desired, the tubular structure 33 may have gas permeable side walls or the side walls may be impermeable and the atmosphere admitted to the testing chamber through a porous membrane 35 in the bottom 36 of the vapor collecting cylinder, see FIGS. 5 and 6.

In alternate forms of the embodiment, a deposited film on a supporting substrate may be used as a collecting material.

Figure 7:
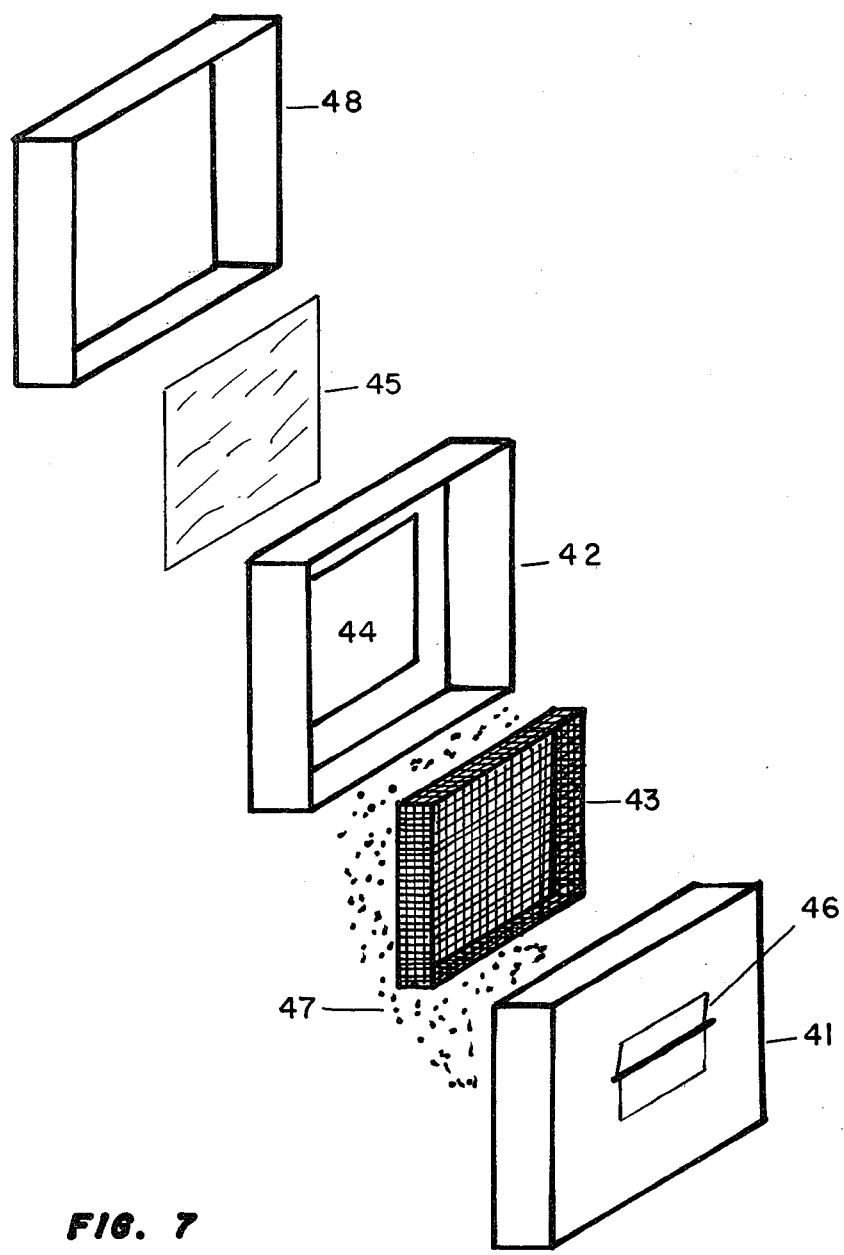
FIG. 7 is an exploded view of a typical adaption of the invention.
Figure 8:
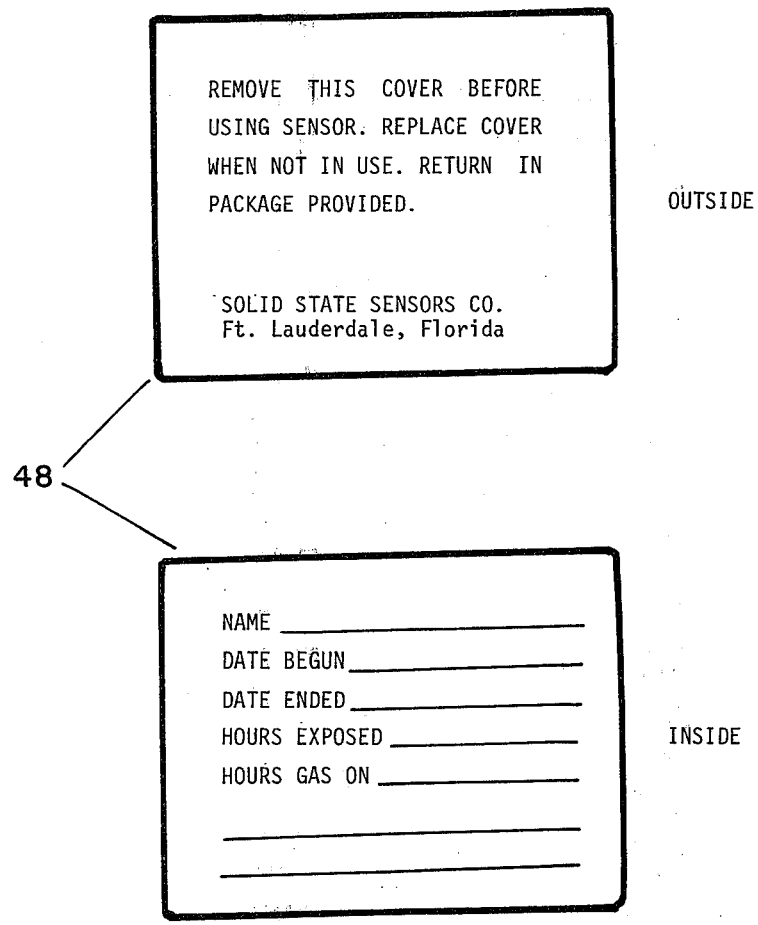
FIG. 8 is a cover for the embodiment of FIG. 7.

FIG. 7 illustrates an adaptation of the principles previously described herein. In this system, a rectangular container comprised of a rear tray 41 and a cover 42 is adapted to house a wire basket 43 which contains an adsorbent sensitive to a material to be monitored. The cover 42 includes an opening 44 which is sealed by a porous membrane 45 constructed from a material which will permit passage of the material to be detected. The container 41 has a clip 46 affixed to the back so that a person may attach the device to their clothing. In operation, an adsorbent for materials which are to be detected is placed within the receptacle part of the wire basket 43. It is placed within the container and covered with protective granular adsorbent 47 which passes the material to be monitored but adsorbs interfering elements and sealed with container 42. A cover 48 is placed over container cover 42 to prevent the atmosphere from entering the test chamber until it is desired that a monitoring period is to begin. The cover 48 may include instructions such as illustrated in FIG. 8 whereby a user is directed to remove the cover before using the sensor and to replace the cover when the sensor is not to be used and when the container is returned to a processing lab for analysis. The inside of the cover 48 as illustrated in FIG. 8 may contain information relative to the exposure.

Figure 9:
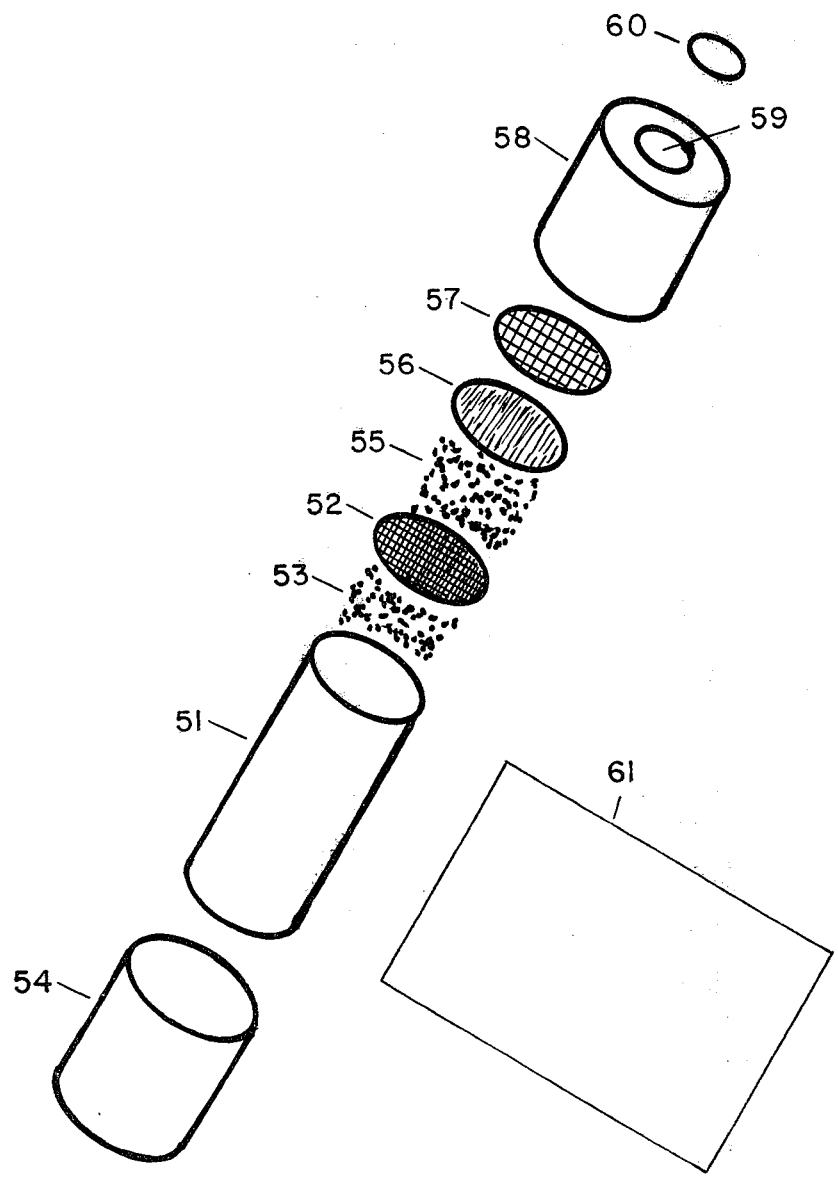
FIG. 9 is an exploded view of a tubular adaptation of the invention.

The exploded view of FIG. 9 represents one embodiment of the present invention which utilizes a tubular structure. In this embodiment, a tubular section 51 is divided by a screen 52 which forms an upper and lower chamber. The lower chamber contains a granular adsorbent 53 which functions to adsorb the specific material being monitored. The adsorbent 53 is contained within the tubular structure by cap 54.

A second adsorbent 55 is deposited in the upper portion of tubular member 51 on top of separating screen 52. This adsorbent will not adsorb the material being monitored but it will adsorb other constituents in the ambient atmosphere which may interfere with the adsorbent 53. A porous membrane 56 is placed over the adsorbent 55 to regulate the flow of atmosphere into the tubular system 51. Membrane 56 and the adsorbent 55 therebelow is secured in place by a screen member 57 which is held in place by a cap 58.

Cap 58 has an aperture 59 located in the upper portion which is dimensioned to permit a calculated exposure to the atmosphere so that the rate of adsorption of the material being monitored by adsorbent 53 may be determined after a period of exposure by driving off the materials from the adsorbent 53 and measuring the amount of materials which were adsorbed. An adhesive disc or cap 60 is used to seal the opening 59 so that the monitoring system will be inactive until its use is desired.

A label 61 similar to that illustrated in FIG. 8 may be provided to supply test data. This label, 61, is wrapped about the cylinder 51 after caps 54 and 58 are in place and functions as a sealing means to ensure that both caps are not removed during the normal use of the monitoring device.

The following are various methods utilizing the inventive concepts for monitoring noxious materials in the atmosphere:

METHOD 1

The system may be employed in a method to detect nitrous oxide as follows:

1. A two piece metal or plastic container is prepared with a hole in the container. The size of the hole is dimensioned to control the rate of vapor collected.

2. The hole is covered with a chemically inert membrane such as teflon (PTFE), silicone, or other materials, as long as they are porous, and allow diffusion of nitrous oxide.

3. A rectangular wire mesh basket is prepared with one end open. The wire mesh basket functions as a container to hold an adsorbent nitrous oxide.

4. The nitrous oxide adsorbent such as a "13×" molecular sieve produced by Davison Chemical Company is cleaned by heating it for at least one hour at a maximum temperature of between 300° and 450° Celsius at a pressure of $10^{-3}$ torr.

5. The molecular sieve or adsorbent is added to the basket, and the open end is closed with a wire mesh flap.

6. The basket containing the adsorbent sieve is fastened to the bottom of the container, using an adhesive or solder, or the sieve may be contained in a place that is an integral part of a molded container.

7. A drying agent such as magnesium chloride is packed around the basket containing the sieve.

8. The top of the container, with the porous membrane attached, is placed over the bottom part, and the two pieces are sealed so that the only way for vapor to contact the adsorbent sieve is for it to be transported through the porous membrane and drying agent.

9. A tight fitting cover is placed over the part of the container that contains the membrane.

10. A nitrous oxide sensor is attached to the clothing of a person with a clasp and at the beginning of the monitoring period, the tight fitting cover is removed.

11. The sensor is exposed during the monitoring period and after the period is over, the tight fitting cover is replaced.

12. Data on an identity of user, date, exposure time, and other information is recorded on a label that is affixed to the sensor.

13. The detector is placed in a container, and returned to a place where the amount of nitrous oxide collected on the adsorber is measured.

14. The sieve or nitrous oxide adsorbent is placed in an analysis system.

15. The adsorbent is heated until all of the nitrous oxide is desorbed.

16. The desorbed nitrous oxide is caused to flow through a detector cell which provides an indication of the absolute amount of nitrous oxide freed from the collector and thus provides an indication of the rate of adsorption of nitrous oxide and the amount in the atmosphere which was monitored.

17. As an alternate extraction method, nitrous oxide may be removed from the adsorbent by the use of a suitable solvent.

METHOD 2

A method for monitoring ethylene oxide consists of the following:

1. A container is prepared by placing a thin piece of metal or a substrate having a film deposited thereon in the bottom portion of the container. The metal or film is any material that adsorbs ethylene oxide such as one of the transition metals (Ni, Cr, Va).

2. The adsorbing surface is covered by a granular adsorbent which will not adsorb ethylene oxide but will adsorb other constituents of the atmosphere which will affect the ability of the adsorbing surface to collect ethylene oxide.

3. A cover having an aperture closed with a porous membrane is placed over the container to retain the adsorbers. The size of the hole in the porosity of the membrane are selected to control the rate of adsorption of ethylene oxide.

4. The sensor is exposed to ambient atmosphere for a desired period of time, after which it is sealed and forwarded to an analysis facility.

5. At the analysis facility, an infrared analysis technique is utilized wherein the ethylene oxide is desorbed from the surface and the vapor is irradiated by an infrared system of a predetermined wavelength. The amount of released ethylene oxide is determined by measuring the infrared adsorption of the vapor to provide an absolute value of the amount collected during the exposure period.

6. An alternate method of determining the amount of ethylene oxide adsorbed may be the direct analysis of the surface through irradiation techniques whereby the reaction of the surface to specific wavelengths will provide an indication as to the amount of ethylene oxide contained thereon.

METHOD 3

Nitrous oxide may be sensed as follows:

1. An adsorbent material for nitrous oxide such as a metal film, a molecular sieve, or charcoal is placed in the bottom of a container.

2. A retaining screen is placed over the adsorbent and a drying agent such as magnesium perchlorate $[Mg(ClO^4)_2]$, magnesium chloride $[MgCl_26H_2O]$, or other drying agent is placed over the screen and the container is sealed with a cover having an opening over which a porous membrane is provided which will retain the drying agent and permit transportation of vapor therethrough.

3. The atmosphere to be monitored is permitted to pass through the porous membrane and drying agent wherein nitrous oxide may then be adsorbed by the adsorbent.

4. The amount of nitrous oxide collected by the adsorbent is determined by any one of the number of well known techniques.

METHOD 4

The amount of ethylene oxide in the atmosphere may be determined by follows:

1. An adsorbent for ethylene oxide is placed in a container and covered with a screen device to secure the adsorbent in the bottom of the container.

2. Activated alumina or other adsorbent that adsorbs alcohol vapor but does not adsorb ethylene oxide is placed on top of the screen and the container is closed by a cover having an opening secured with a porous membrane which will contain the activated alumina.

3. The container is exposed to the ambient atmosphere for a predetermined period of time.

4. The ethylene oxide adsorbent is removed and the ethylene oxide is driven off in a test system which will measure the amount of ethylene oxide to provide an absolute value from which the amount of ethylene oxide in the monitored atmosphere may be determined.

While preferred embodiments of this invention have been illustrated and described, variations and modifications may be apparent to those skilled in the art. Therefore, I do not wish to be limited thereto and ask that the scope and breadth of this invention be determined from the claims which follow rather than the above description.

What I claim is:

1. A monitoring device, comprising:
   a primary adsorbent for a predetermined substance;
   a gas permeable basket for containing said primary adsorbent;
   means to secure said basket in said container;

means for admitting ambient atmosphere into said container; and an isolating granular adsorbent for selectively removing material from the atmosphere by adsorption, said isolating adsorbent positioned in said container between said primary adsorbent and said means for admitting ambient atmosphere whereby ambient atmosphere can reach said primary adsorbent only after flowing through said isolating granular adsorbent arranged in a bed of loosely packed granules.

2. A monitoring device as defined in claim 1 wherein said primary adsorbent is charcoal.

3. A monitoring device as defined in claim 1 wherein said primary adsorbent is a metal film.

4. A monitoring device as defined in claim 1 wherein said primary adsorbent is a transitional metal.

5. A monitoring device as defined in claim 1 wherein said primary adsorbent is a molecular sieve.

6. A monitoring device as defined in claim 1 wherein said isolating adsorbent is magnesium perchlorate.

7. A monitoring device as defined in claim 1 wherein said isolating adsorbent is magnesium chloride.

8. A monitoring device as defined in claim 1 wherein said container is a rectangular box and said means for admitting ambient atmosphere is a cover for said box including an aperture dimensioned to control the rate at which ambient atmosphere enters said container and said aperture is sealed with a gas permeable membrane.

9. A monitoring device as defined in claim 8 wherein said gas permeable membrane is adapted to permit passage of said predetermined substance.

10. A monitoring device as defined in claim 8, further comprising a gas permeable barrier adapted to hold said primary adsorbent in the section of said container opposite said cover.

11. A monitoring device as defined in claim 1, wherein said primary adsorbent is in the form of a solid cylindrical body.

12. A monitoring device as defined in claim 1 wherein said means for admitting ambient atmosphere into said container is an aperture of a predetermined size calculated to admit a predetermined volume of gas into said container over a predetermined period of time.

13. A monitoring device as defined in claim 1 wherein said means for admitting ambient atmosphere into said container comprises a membrane which selectively passes said predetermined substance and resists the passage of substances not being monitored.

14. A monitoring device, comprising:
a container formed in the shape of a tubular structure;
means to close one end of said tubular structure;
a primary adsorbent for a predetermined substance;
a gas permeable disc for holding said primary adsorbent in the closed end of said tubular structure;
an isolating granular adsorbent for selectively removing material from the atmosphere;
a gas permeable diaphragm for holding said isolating granular adsorbent between the open end of said container and said gas permeable disc;
a screen member for securing said gas permeable membrane at the open end of said container; and
a cover for the open end of said container including an opening in said cover dimensioned to permit ambient atmosphere to enter at a predetermined rate.

15. A method for determining the exposure of an individual to toxic material in the form of a substance or vapor, including the steps of:
placing a primary adsorbent for said toxic material in a container closed at one end and open at an opposite end;
isolating said primary adsorbent from ambient atmosphere by encasing said primary adsorbent in an isolating granular adsorbent; and passing a gas sample through said isolating granular adsorbent to said primary adsorbent.

16. A method as defined in claim 15 wherein said step of passing a gas sample through said isolating granular adsorbent to said primary adsorbent includes the steps of:
removing materials other than said toxic materials from said gas sample with said isolating granular adsorbent; and
adsorbing said toxic materials in said gas sample with said primary adsorbent.

17. A method as defined in claim 15 further comprising the steps of:
removing said primary adsorbent from said container;
driving off said toxic substance from said primary adsorbent; and
measuring the amount of said toxic substance driven off of said primary adsorbent.

* * * * *